US011109999B2

(12) United States Patent
DeMore, Jr. et al.

(10) Patent No.: US 11,109,999 B2
(45) Date of Patent: Sep. 7, 2021

(54) DEVICE FOR REMOVING HEAT, ENERGY, AND/OR FLUID FROM A LIVING MAMMAL

(71) Applicant: CoolTech, LLC, Baltimore, MD (US)

(72) Inventors: William G. DeMore, Jr., Laurel, MD (US); James A. Kendall, Frederick, MD (US); Benjamin R. Lane, Hydes, MD (US); Chester B. Larrow, Baltimore, MD (US); Kun Li, Baltimore, MD (US); Brian L. Lipford, Bel Air, MD (US); Owen J. Lu, Dayton, MD (US); Joshua M. Mull, Baltimore, MD (US); Aaron S. Pearl, Marlborough, MA (US)

(73) Assignee: COOLTECH, LLC, Baltimore, MD (US)

( * ) Notice: Subject to any disclaimer, the term of this patent is extended or adjusted under 35 U.S.C. 154(b) by 14 days.

(21) Appl. No.: 16/047,136

(22) Filed: Jul. 27, 2018

(65) Prior Publication Data
US 2020/0030139 A1 Jan. 30, 2020

(51) Int. Cl.
*A61F 7/12* (2006.01)
*A61F 7/00* (2006.01)
*A61M 16/06* (2006.01)

(52) U.S. Cl.
CPC ............. *A61F 7/12* (2013.01); *A61F 7/0085* (2013.01); *A61M 16/0666* (2013.01); *A61F 2007/0006* (2013.01); *A61F 2007/006* (2013.01); *A61F 2007/0063* (2013.01); *A61F 2007/0065* (2013.01); *A61F 2007/0068* (2013.01); *A61F 2007/0076* (2013.01)

(58) Field of Classification Search
CPC ... A61F 7/12; A61F 7/0085; A61F 2007/0065
See application file for complete search history.

(56) References Cited

U.S. PATENT DOCUMENTS

| 2,895,685 | A | 7/1959 | Peeps |
| 6,740,058 | B2 * | 5/2004 | Lal ...................... A61F 9/00745 604/65 |
| 7,318,437 | B2 * | 1/2008 | Gunaratnam ..... A61M 16/0644 128/206.11 |
| 8,480,723 | B2 | 7/2013 | Barbut et al. |
| 2008/0051674 | A1 * | 2/2008 | Davenport ............. A61B 5/087 600/561 |

(Continued)

FOREIGN PATENT DOCUMENTS

WO 2017/020898 2/2017

OTHER PUBLICATIONS

International Search Report issued in co-pending application No. PCT/US2019/043593 dated Jan. 7, 2020.

*Primary Examiner* — Kaitlyn E Smith
(74) *Attorney, Agent, or Firm* — Whiteford, Taylor & Preston, LLP; Peter J. Davis

(57) ABSTRACT

The present invention provides improved devices for removing energy and fluid from body fluid containing spaces and surfaces of a mammal, the devices including isolated air and water delivery systems configured to simultaneously deliver streams of dry air and liquid water to the nostrils of a patient, without allowing the streams to come into contact with one-another until it enters the patient's nostrils.

12 Claims, 15 Drawing Sheets

(56) References Cited

U.S. PATENT DOCUMENTS

| | | | |
|---|---|---|---|
| 2010/0252041 A1* | 10/2010 | Kapust | A61M 16/0622 |
| | | | 128/204.23 |
| 2010/0252042 A1* | 10/2010 | Kapust | A61M 16/101 |
| | | | 128/204.23 |
| 2011/0209709 A1* | 9/2011 | Davidson | A61M 16/06 |
| | | | 128/205.25 |
| 2012/0083764 A1* | 4/2012 | Barbut | A61F 7/12 |
| | | | 604/514 |
| 2012/0167878 A1* | 7/2012 | Belson | A61M 19/00 |
| | | | 128/200.16 |
| 2014/0261433 A1* | 9/2014 | Guney | A61M 16/06 |
| | | | 128/205.25 |
| 2015/0196726 A1* | 7/2015 | Skipper | A61M 16/20 |
| | | | 128/202.27 |
| 2015/0250646 A1* | 9/2015 | Lipford | A61F 7/12 |
| | | | 424/613 |
| 2016/0114118 A1* | 4/2016 | Gunaratnam | A61M 16/0833 |
| | | | 128/202.27 |
| 2017/0027745 A1 | 2/2017 | Rozenberg et al. | |
| 2017/0028153 A1* | 2/2017 | Judson | A61M 16/0666 |
| 2018/0153737 A1 | 6/2018 | Harikrishna et al. | |

\* cited by examiner

DEVICE FOR REMOVING HEAT, ENERGY, AND/OR FLUID FROM A LIVING MAMMAL

BACKGROUND OF THE INVENTION

1. Field of the Invention

The invention relates generally to methods and devices for removing heat, energy, and/or fluid from a living mammal.

2. Background Information

Methods and devices for non-invasive anatomical and systemic cooling and neuroprotection are disclosed in U.S. patent application Ser. Nos. 13/579,370 and 14/578,094.

SUMMARY OF THE INVENTION

The present inventions include improvements to the devices disclosed in U.S. patent application Ser. No. 13/579,370 and U.S. patent application Ser. No. 14/578,094, the disclosures of which are incorporated herein in their entirety.

Evaporative cooling is a physical phenomenon in which the evaporation of a liquid results in the cooling of an object or a liquid in contact with it, due to the fact that it requires heat or energy to change a liquid into a gas. The amount of energy required to change a liquid to a gas is directly proportional to the total mass of liquid that is changed to a gas and the enthalpy of vaporization. Enthalpy of vaporization, also referred to as latent heat of vaporization, is the amount of energy required to transform a given quantity of a substance from a liquid into a gas. Different liquids have different enthalpies of vaporization.

The present invention makes use of this phenomenon to achieve energy and fluid removal from the human body. According to the invention, dry air is blown across a patient's nasal turbinates which promotes the evaporation of liquid water in and on the nasal turbinates. The heat or energy needed to vaporize the water is extracted from the host surface and transported out of the body. According to a preferred embodiment, a supply of misted water, preferably saline solution, is provided to the nose without being exposed to the dry air stream prior to the point of delivery at the entrance to the patient's nose. The supplied saline solution is used to both support or augment the evaporative heat transfer process (supplementing the body's naturally occurring water generating mucus membranes), and to help reduce or eliminate the potential to desiccate the local tissue in the air pathway if the patient's native water is evaporated from the patient's body during the process.

The dry air stream and the water is provided to the patient via isolated delivery paths using a specially designed device, tubes, and mask which deliver the dry air and the water to the patient at a delivery point at or just inside the nostril openings, up to which point the separate dry air and water flow paths have been kept isolated from one-another. No portion of the device is required to be inserted into the nasal cavity.

According to various aspects of the invention, therefore, there is provided a method and an improved device for removing heat and/or other energy from a mammal; cooling an anatomical feature in a mammal (e.g., preferential brain cooling), providing systemic cooling in a mammal, removing excess fluid from a mammal, raising the metabolic rate of a mammal, promoting weight loss in a mammal, prevention of esophageal burn-through during catheter ablation treatment for atrial fibrillation, reduction or inhibition of β-amyloid accumulation in a mammal, amelioration of pain due to migraine, amelioration of insomnia, and/or delay in onset or amelioration of senile dementia and/or Alzheimer's in a human, by controlled, induced evaporation of a bodily fluid from a bodily fluid-containing space or surface, such as the nasal turbinates of a mammal. The method includes simultaneously delivering isolated flows of a dry gas (compressed or not) which does not include a coolant (i.e., a refrigerant or chilled gas or vapor) with or without water into or upon the bodily fluid-containing space or surface to provide controlled evaporation and transport (removal) of the bodily fluid upon contact with the dry gas. Such evaporation and transport of the bodily fluid removes heat, energy and fluid from the body.

The device is configured to be lightweight and portable, and may be configured to operate via connection to standard wall socket and/or optionally by onboard rechargeable battery.

The device draws air from either the ambient room through a filtered inlet plenum or from a hospital wall pressurized air source through an inlet valve and dries the air for delivery to the patient. Once inside the device, the air path passes through an inlet plenum pathway, a bulk plenum pathway, a desiccant cartridge, a heat sink, across various sensors and out an air outlet. While inside the device the airflow path is isolated from entrance to exit. The device also has a separate water delivery system which keeps the water flow path isolated from the air flow path. The water delivery system includes a water supply tube fitted with a saline bag spike at one end, continuously passing through a water/air manifold cartridge, and ending at misting nozzles at the other end. The water/air manifold cartridge has a dual function of interfacing the water supply tube with a peristaltic pump in the device, and combining the isolated water and air delivery paths into an integrated tube set but which maintains separately the isolation of the water and air supply lines.

According to a preferred embodiment, the device according to the invention has a portable housing having an air inlet and air outlet connected by an air flow path through the device, a fan situated in the housing to draw air from an air supply through the air inlet, through the air flow path and out the air outlet into an air delivery tube, a single use replaceable desiccant cartridge situated in the air flow path to dry the air, a heat sink to remove heat generated as a byproduct of extracting moisture from the air stream, a peristaltic rotary fluid pump situated in the housing to draw fluid from an independent fluid supply through a fluid supply line and deliver it to the patient through an isolated fluid delivery line. The device also includes temperature, humidity, pressure, and flow sensors as well as inputs for patient temperature sensors, and one or more batteries along with standard connections for wall power (110V-240V). In addition, the device interface may be configured to allow an operator to manually select the dosing level, which will set the air flow rate (from low to high, in multiple increments). The device may also be used in a closed-loop control mode, with a proportional-integral-derivative (PID) control system (processor/controller and software), that allows the operator to set a target body temperature for the patient. According to this embodiment, the device has an input port for receiving a patent temperature monitor output plug that allows the patient's temperature to be continuously fed into the device. The PID control system can be set to automatically control the air flow to the patient, generally with high air flow during the initial temperature ramp down period, and then reduced air flow to maintain the target temperature once reached. The PID controller monitors and sets air flow supplied to the patient using three separate inputs: pressure of the air supplied to the patient, temperature of the air supplied to the patient, and the air flow rate itself. The PID control system monitors each of these parameters separately to ensure patient safety, e.g., that the supplied air pressure, air temperature, and air flow rate to the patient do not get too high.

According to further preferred embodiments, there is provided according to the invention a replaceable manifold assembly/cartridge configured to be placed into complimentarily shaped interface in a side of the housing in order to engage with the peristaltic water pump and to separately engage with the airflow outlet. The manifold cartridge is attached to/part of an integrated tubeset including an air delivery tube for delivering the dry air to the patient and a water delivery tube for delivering an isolated stream of water to the patient.

At some point before it reaches the patient, the tubeset bifurcates into two sets of air/water delivery tubes, one for each of a patient's nostrils.

At the opposite end of the tubeset, the two sets of air delivery tubes and isolated water delivery tubes contained therein are connected to a specially designed patient interface/delivery apparatus configured to simultaneously delivery separate streams of dry air and water to the patient's nose at the nostril openings.

According to a preferred embodiment of the invention, the patient interface device includes a flexible plastic strip configured to rest on or just above a patient's lip, just beneath the nose, and extending on either side of the nose, resting against the patient's face to a point between the patient's cheek bones and ears. Opposite ends of the strip are connected to an adjustable strap to hold the device to the user's face. The center portion of the bridge defines one or more slots to slidably/adjustably receive the ends of the tubeset to accommodate a range of different distances between the center of the patient's nostrils. The ends of the air tubes are fitted with nasal pillows configured to rest at the entrance of a patient's nostrils. The ends of the water delivery tubes are fitted with nozzles, which are located primarily inside the nasal pillows and partially extending outward (a few millimeters) from the center of the nasal pillow air outlets so that the water stream and the air stream are completely isolated from one-another until the point of delivery in the nose.

No portion of the device covers the user's chin, jawline, or mouth, or any part of the user's nose except the nostrils.

The invention is particularly well suited to use in ambulatory therapies, including emergency settings, combat settings, sport settings, and even clinic and home-use settings.

BRIEF DESCRIPTION OF THE DRAWINGS

Various features and advantages of the disclosure will become more apparent by the following detailed description of several embodiments thereof with reference to the attached drawings, of which.

DETAILED DESCRIPTION OF THE INVENTION

Figure 1:
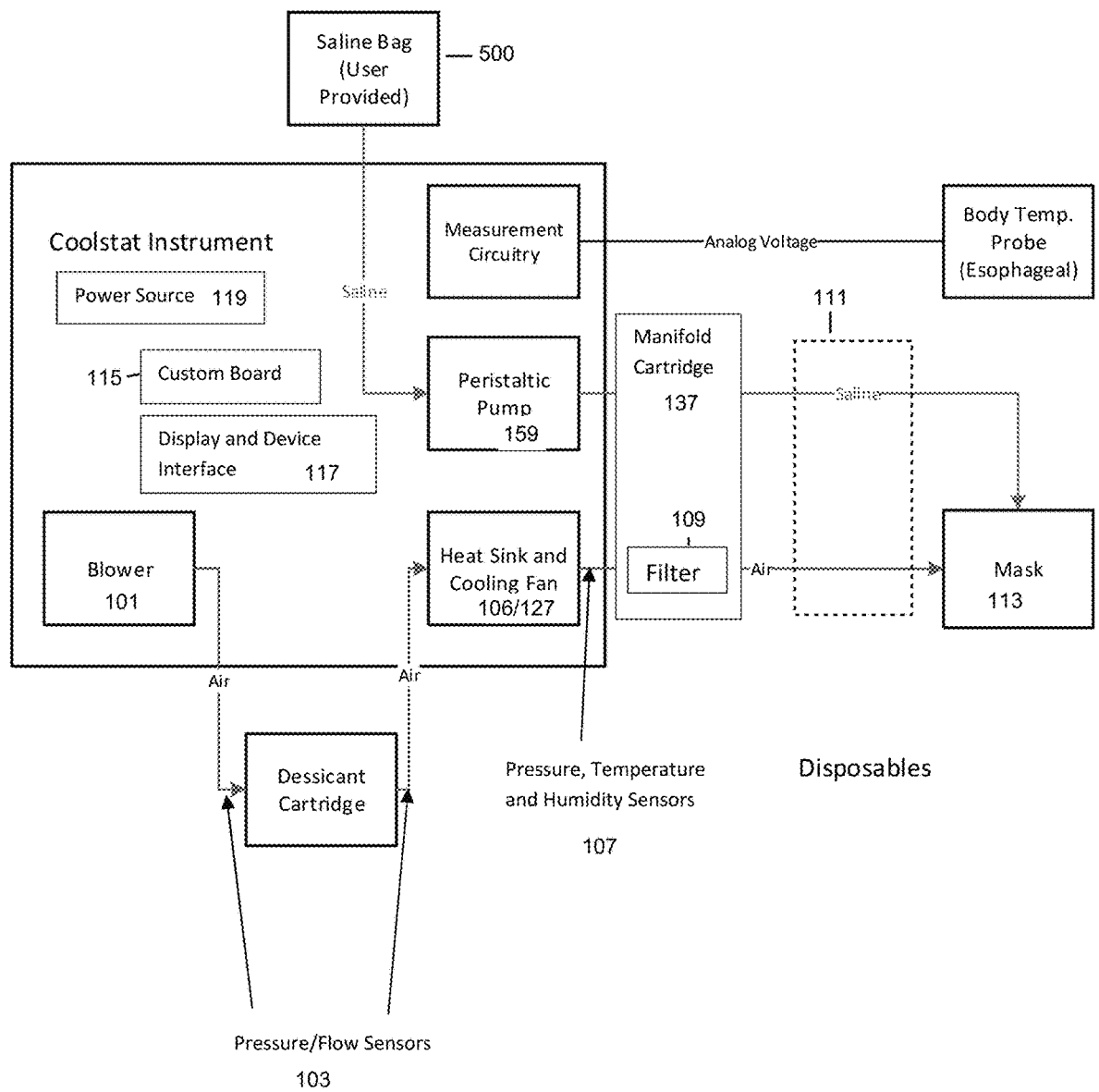
FIG. 1 is a schematic of a device according to an embodiment of the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used herein, "relative humidity" is used to refer to the amount of water vapor that exists in a gaseous mixture of gas and water vapor as a function of its current state, for example temperature. Essentially, relative humidity is a measure of the amount of moisture in the air compared to what the air is capable of holding at a given temperature and pressure. In various embodiments, the relative humidity of the gas before being contacted with a bodily fluid or delivered misted liquid is less than or equal to about 50, 40, 30, 20, 10, 5 or 0%. In various embodiments, the relative humidity of the gas after being contacted with a bodily fluid is greater than or equal to about 60, 70, 80, 90 or 100%.

As used herein, a "dry" gas is used to refer to a gas that is unsaturated with water vapor or other liquid vapor. In various embodiments, the dry gas has a relative humidity of less than or equal to about 50, 40, 30, 20, 10, 5 or 0%.

Several types of gases are suitable for use with the present invention, specifically those that can induce or enhance an evaporative heat exchange process with the body's existing mucus (water) liquid and/or with other liquids supplied by the invention. Such gases include, but are not limited to air, $NO_2$, $CO_2$, $O_2$, and inert gases, such as He, Ar, and Xe, as well as combinations thereof.

The dry gas delivered according to the invention does not include a coolant. As used herein, the term "coolant" includes volatile gases and may include dry ice, liquid nitrogen, chilled saline, chilled water, anti-freeze solution, refrigerants, such as fluorocarbons, chlorofluorocarbons (CFCs), hydrochlorofluorocarbons (HCFCs), perfluorocarbons (PFCs), R-134a (1,1,1,2 tetrafluoro ethane), Freon™, and other cooling fluids or refrigerants, or a combination thereof. A coolant may also be considered any fluid chilled to a temperature 10° C. or more below normal body temperature. For humans, a coolant would thus be a fluid chilled to about 27, 26, 25, 24, 23, 22, 21, 20, 19, 18, 17, 16, 15, 14, 13, 12, 11, 10, 9, 8, 7, 6, 5, 4, 3, 2, 1, 0° C. or less.

In preferred embodiments of the invention, the dry gas used with the device is air or oxygen, supplied at temperatures from 0° C. up to about 40° C., preferably above 20° C., more preferably at or above 23° C., but in any event no greater than 40° C.

According to a preferred embodiment of the invention, the administration of the dry gas accompanied by the simultaneous delivery of an isolated supply of a liquid to supplements the evaporative heat exchange process inside the body, as well as possibly protecting the body from desiccation. In cases where the liquid is water-based, the added water (supplied by the device) can also be used to help reduce or eliminate the amount of the patient's native water that otherwise would be evaporated from the patient's body during the process, thereby reducing or eliminating a 'desiccating' effect from the evaporative process. Although, in some clinical cases, the goal is to desiccate the patient, i.e., remove water, in which case no added water would be supplied to the patient from the device.

In preferred embodiments of the invention, the liquid will be a saline solution that approximately matches the saline content of the human body, supplied at temperatures from ambient temperature, to normal body temperature (e.g., for humans, 37° C.), and even as warm as a highest clinically acceptable temperature, with liquid at the ambient environmental temperature being particularly suitable for ambulatory settings, especially in emergency contexts. The invention may use liquid temperatures from (ambient temperature) C up to about 40° C., as 40° C. is considered a clinically acceptable temperature.

According to various embodiments, the invention monitors amount of dry gas supplied to the patient's nostrils and simultaneously supplies, via an isolated delivery path and misting nozzles located at the opening of the patient's nostrils, the amount of corresponding liquid needed to support an evaporative heat transfer process. In preferred embodiments of the invention, the gas is air and the liquid is saline, and the amount of saline needed is calculated by the device to match the water carrying capacity of the volume of air being delivered by the device. This is done by measuring the volume of air being delivered, i.e., the air flow rate and time, as well as the temperature and humidity of the air being delivered. The device uses this to calculate the water holding capacity of the supplied air and then delivers a corresponding amount of saline. The amount of liquid supplied can be adjusted by the device to match exactly with the water holding capacity of the air being supplied, or it can be adjusted to supply more or less liquid, depending on the clinical need.

The invention may utilize high flow of gas, which includes flow rates of between about 20 and 200 L/min, between about 40 and 130 L/min, between about 20 and 80 L/min, between about 40 and 500 L/min, between about 100 and 500 L/min, or between about 200 and 500 L/min. For example, gas may be delivered at a flow rate of greater than about 10, 15, 20, 25, 30, 35, 40, 45, 50, 60, 65, 70, 75, 80, 85, 90, 95, 100, 105, 110, 115, 120, 125, and 130 L/min. As discussed herein, the flow rate may be varied throughout the duration of delivery to maximize evaporation within or on the bodily fluid-containing space or surface.

FIG. 1 shows a schematic of a device according to one embodiment of the invention in which air flow is generated by fan/blower 101, and in which the air flow passes through or by air flow sensor 103, disposable/replaceable desiccant cartridge 105, heat sink 106, humidity, pressure and temperature sensor(s) 107, saline bag 500, peristaltic pump 159, manifold cartridge 137. According to the embodiment shown in FIG. 1, after the air has left the device and has moved into the manifold cartridge 137, it passes through disposable filter 109, tubing 111, and nasal mask 113 for delivery to the patient. Flow sensor, heat sink, and/or humidity, temperature and pressure sensors communicate with processor or custom board 115, which in turn drives the display and device interface 117. Power source 119 may be A/C or D/C, and may be supplied by on-board battery or external power source.

Figure 2:
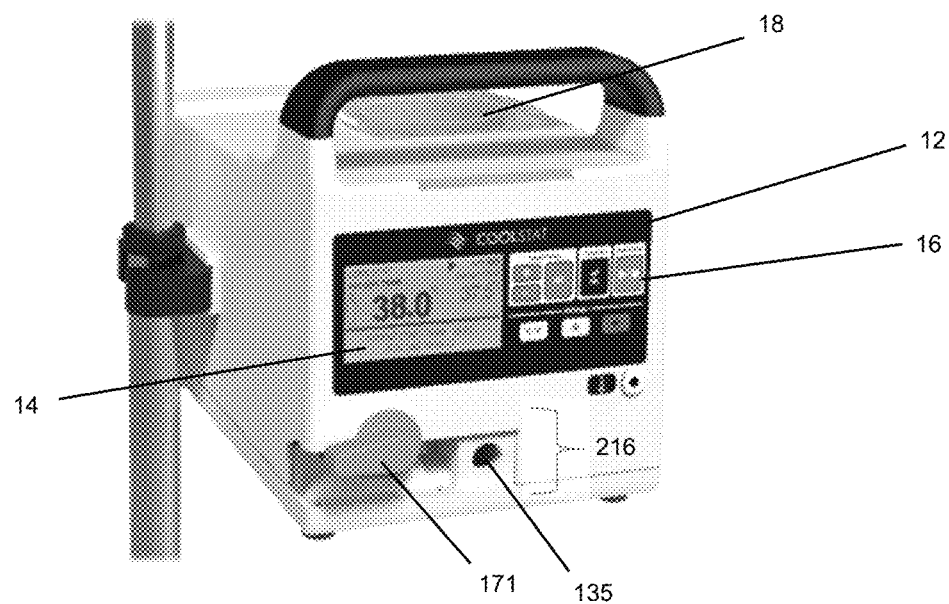
FIG. 2 is a three dimensional perspective representation of a device according to a preferred embodiment of the invention.
Figure 3:
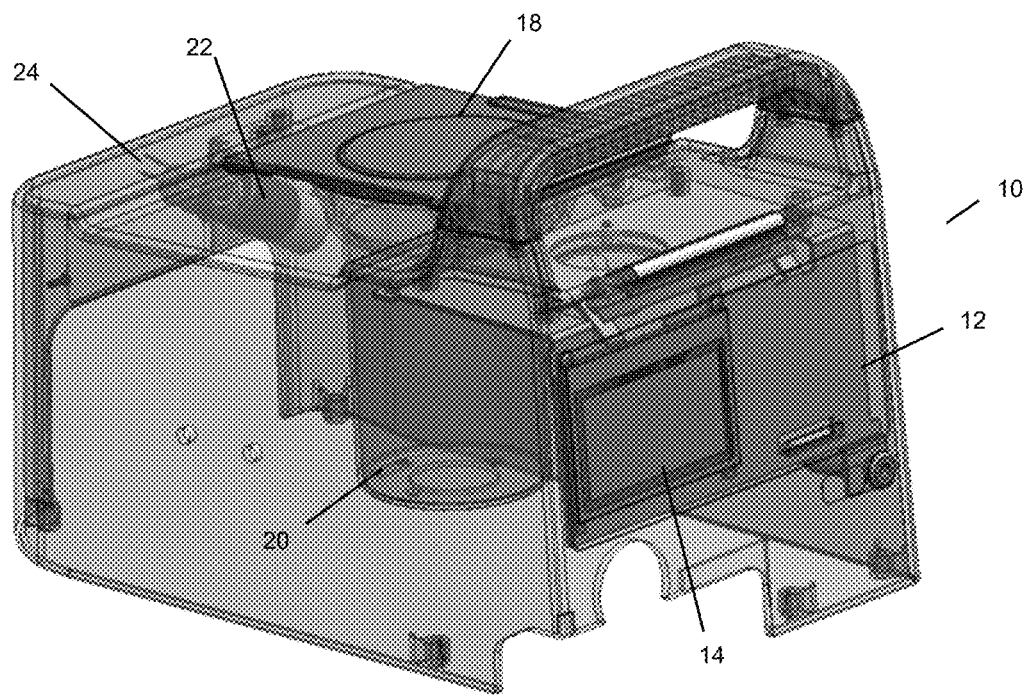
FIG. 3 is a see-through three-dimensional perspective view of a top part assembly of a device according to an embodiment of the invention.
Figure 4:
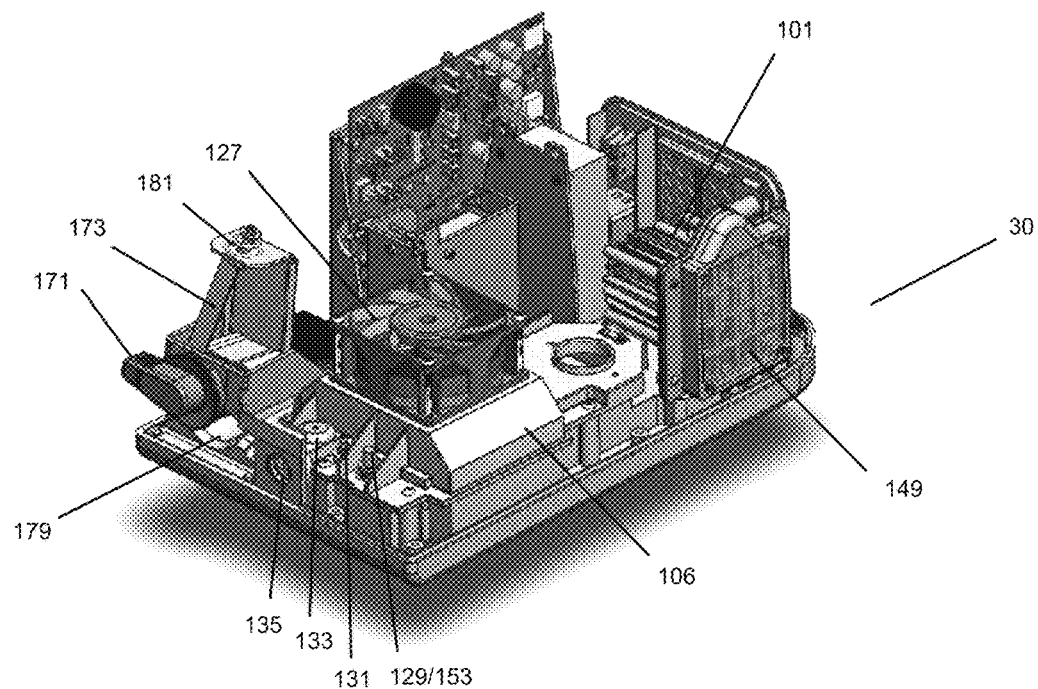
FIG. 4 is a three-dimensional color representation of a bottom part assembly of a device according to an embodiment of the invention.
Figure 5:
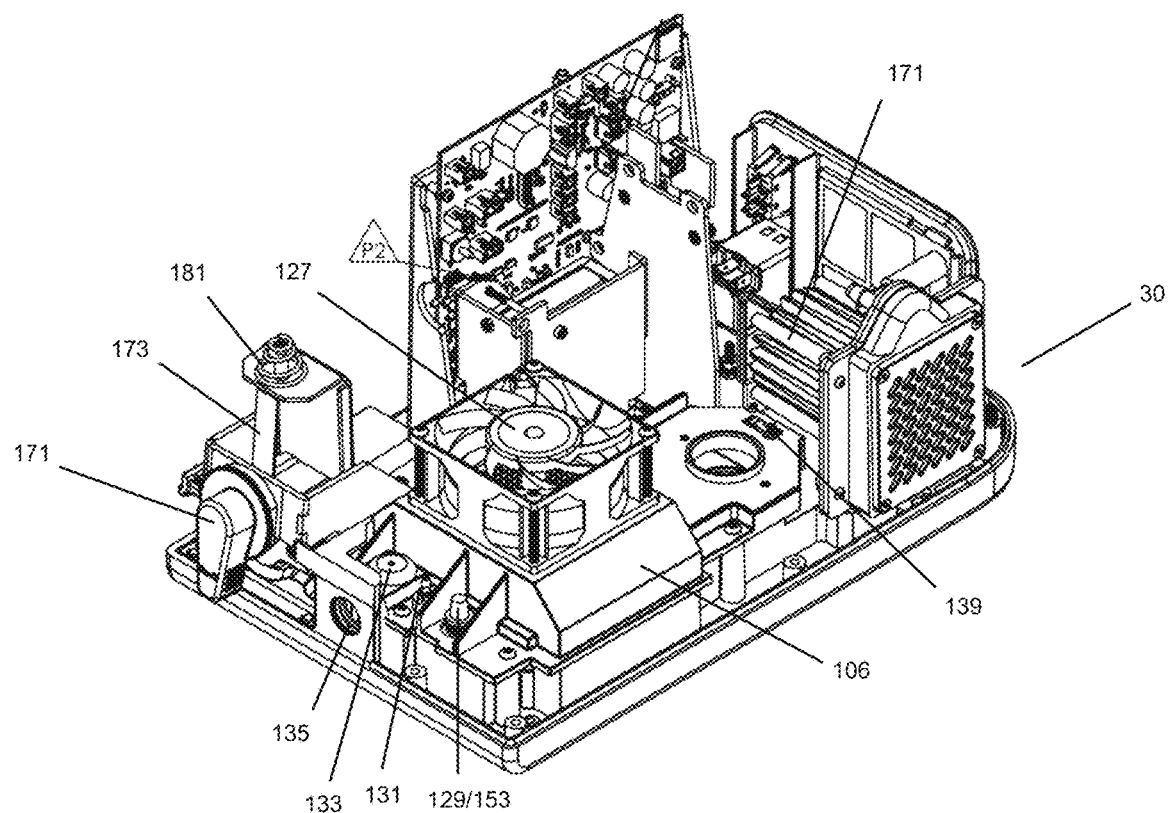
FIG. 5 is a perspective view schematic of a bottom part assembly of a device according to an embodiment of the invention.
Figure 6:
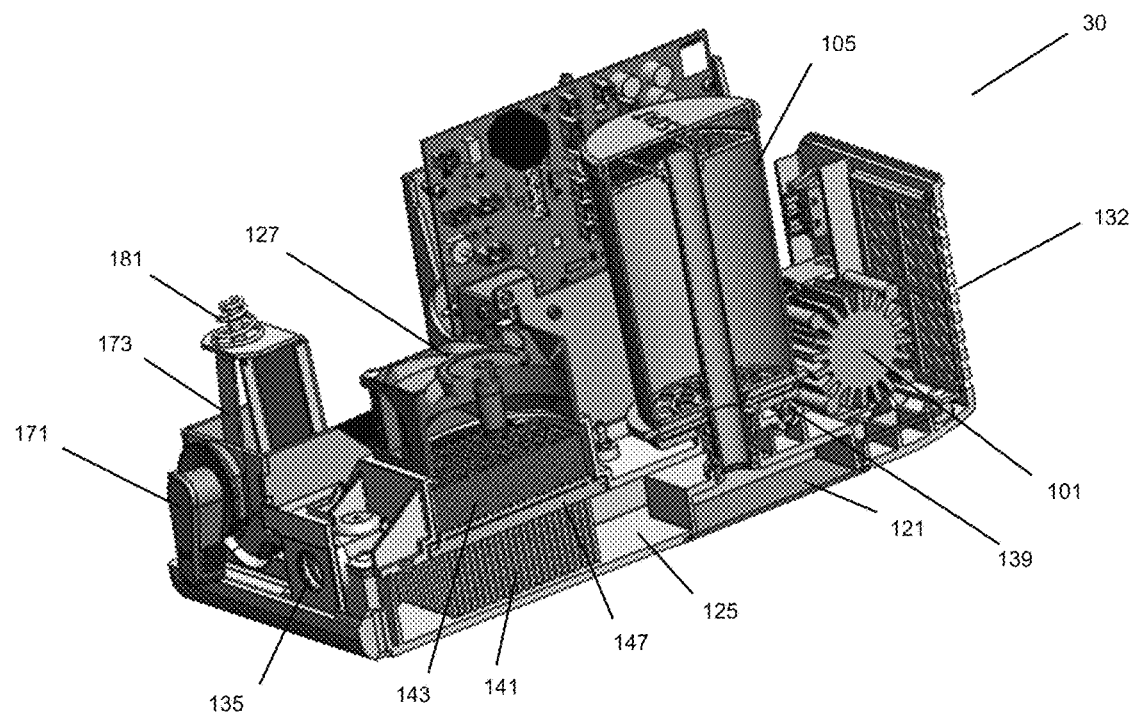
FIG. 6 is a three dimensional color cutaway perspective representation of a bottom part assembly of a device according to an embodiment of the invention.
Figure 7:
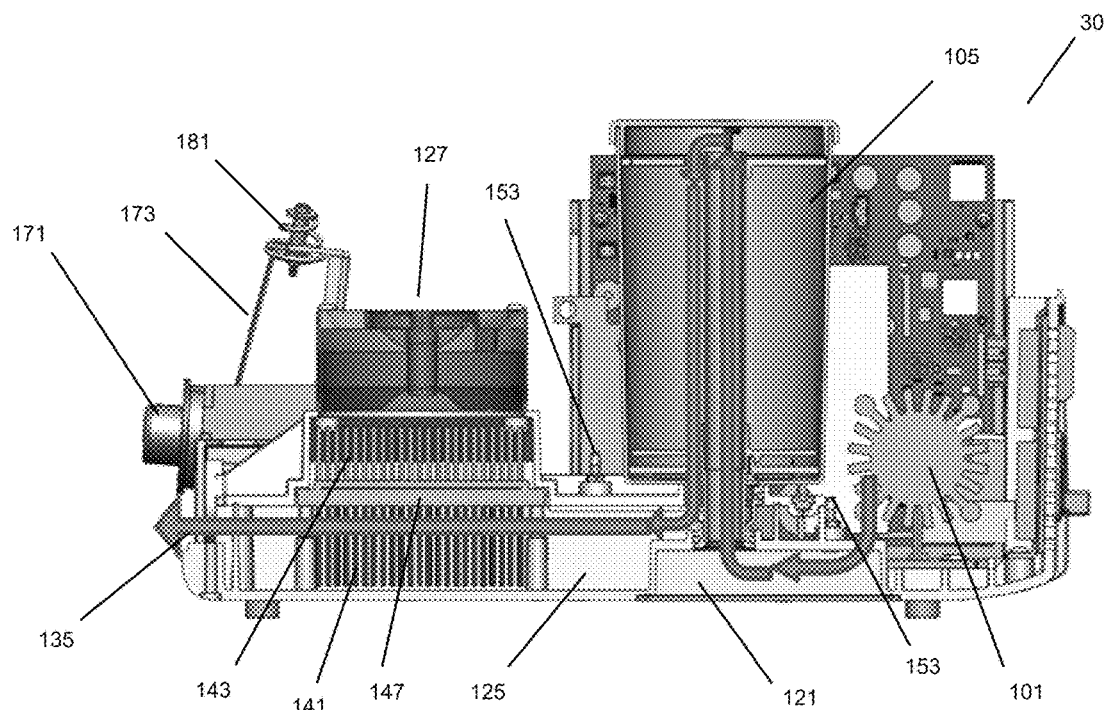
FIG. 7 is a side cutaway view of a bottom part assembly of a device according to an embodiment of the invention.
Figure 10:
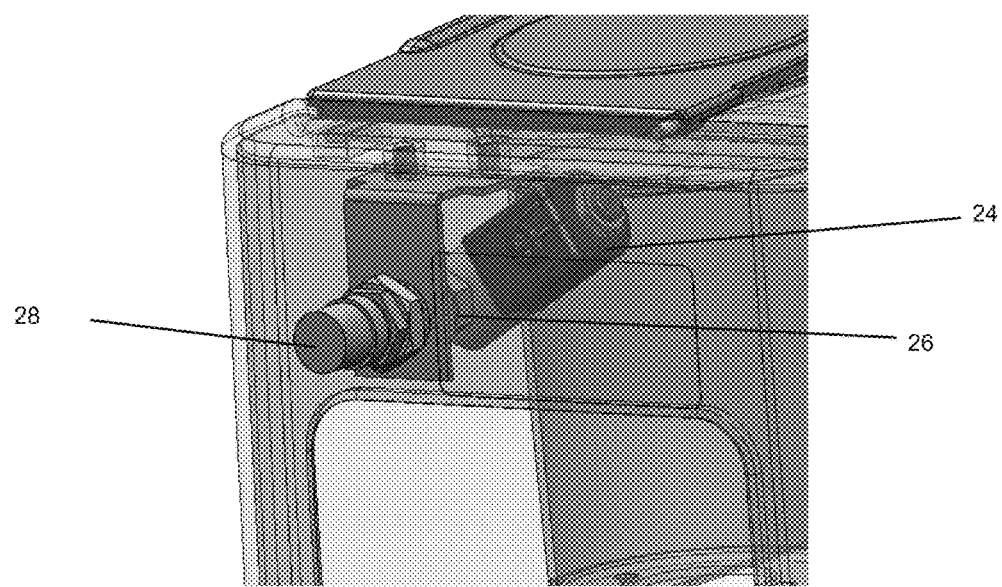
FIG. 10 is a see-through perspective representation of a back-side of a device according to the invention showing a port that is used to interface with hospital-supply gas.
Figure 11:
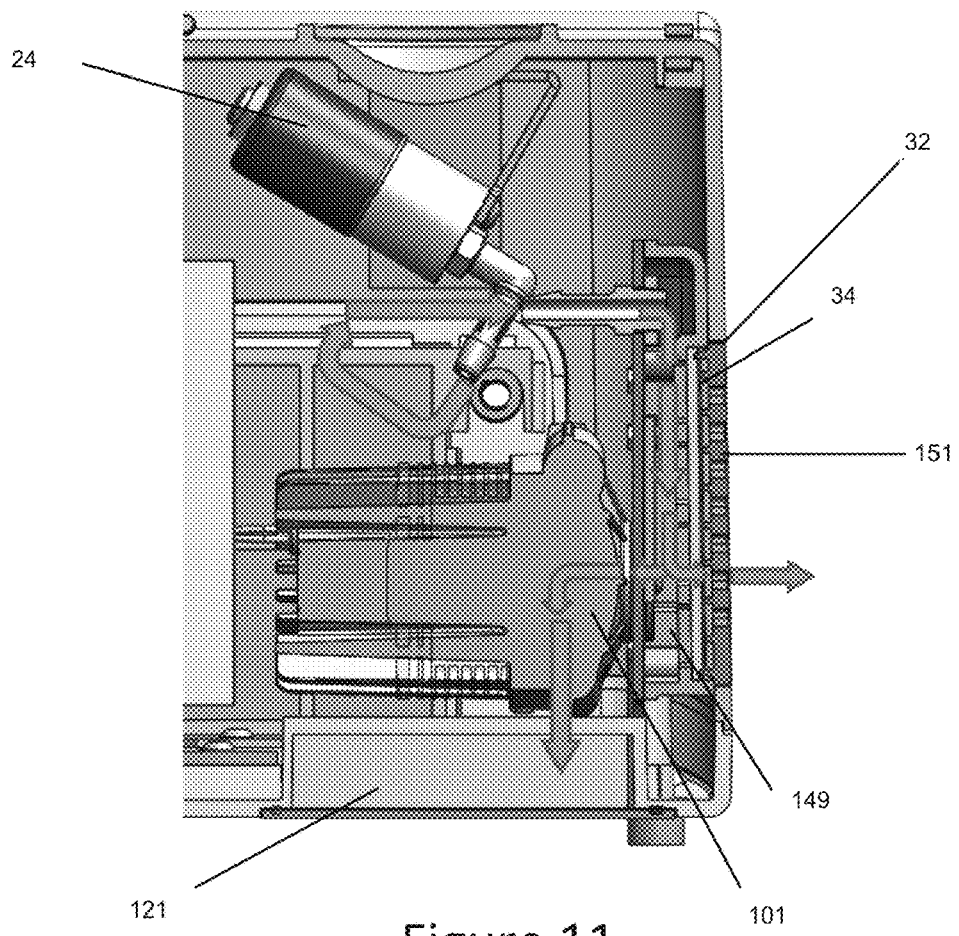
FIG. 11 is a close-up view of a right side portion of the view shown in FIG. 9, with arrows showing the air flow when the device is hooked up to a hospital/pressurized gas source through the gas port.

FIG. 2 shows a representation of a portable device according to an embodiment of the invention. The device will be located next to the patient when in use and will either be mounted on an IV pole or placed on a horizontal surface. The device is comprised of multiple subassemblies which can be assembled largely independently. At the highest level, the device consists of top and bottom subassemblies 10, 30, respectively, which contain all other subassemblies. FIG. 3 shows the top subassembly 10 which includes a user interface 12 which consists of a LCD screen 14 and a membrane panel 16, a hatch 18 and a compartment 20 for receiving the desiccant cartridge 105, and an inlet 26 (See FIG. 10) and valve 24 for hospital wall pressurized air supply (when available). The device bottom subassembly 30, shown, inter alia, in FIGS. 4-7, contains the airflow subassembly, the fluid pump assembly, and the main electrical subassembly.

The airflow subassembly includes the following parts; air inlet 32, inlet plenum 149, inlet filter 34, pressurized air inlet 26 and valve 24, blower/fan 101, blower plenum 121, desiccant cartridge 105, desiccant filter 123, intermediate plenum 125, heat sink 106 and heat sink fan 127, pressure sensors 129, temperature sensors 131, humidity sensors 133 and air outlet 135.

Air is driven through the system by the centrifugal blower 101. The air enters the device either through an inlet 32 and filter 34 in the side of the device or through an inlet 26 and valve 24 for pressurized hospital wall air and exits into an open air inlet plenum 149 where the blower 101 creates suction. The air then enters the blower 101 and exits into a small chamber/blower plenum 121 in the base plate, which leads into the desiccant cartridge 105. The air is dried as it flows through the desiccant cartridge 105, which contains a molecular sieve material that adsorbs water. A high efficiency bacterial/viral filter 123 is included at the outlet of each desiccant cartridge 105 in order to protect the patient from any contaminates, debris, or dust in the desiccant cartridge or the incoming air stream. The air then moves into a larger chamber/intermediate plenum 125 and past the heatsink 106, before passing by an array of sensors and out into the disposable manifold 137.

In an alternative embodiment of the device, the dry gas will have a separate path where it is driven through the device and supplied to the patient only by means of a high pressure of gas supplied from an outside source, such as a tank of air or oxygen, or the wall port of a room in the hospital. In this embodiment, the supplied air enters the device through an inlet 26 and runs through one or more pressure regulators and/or valves that are used to regulate the pressure of the dry gas, such as air or oxygen, down to a level that is appropriate and safe to deliver to the patient. The supplied air will still run through the desiccant cartridge 105, which contains a molecular sieve material that adsorbs water, as well as a high efficiency bacterial/viral filter 123. The supplied air may also still run through the fan 101 though that fan will be powered off during use with the pressurized gas source. As part of this embodiment, the device will recognize when the high pressure supply of gas is turned off or disconnected, at which point the device will automatically start and run the centrifugal fan 101, which will then provide the motive force to supply a flow of dry gas to the patient.

Figure 8:
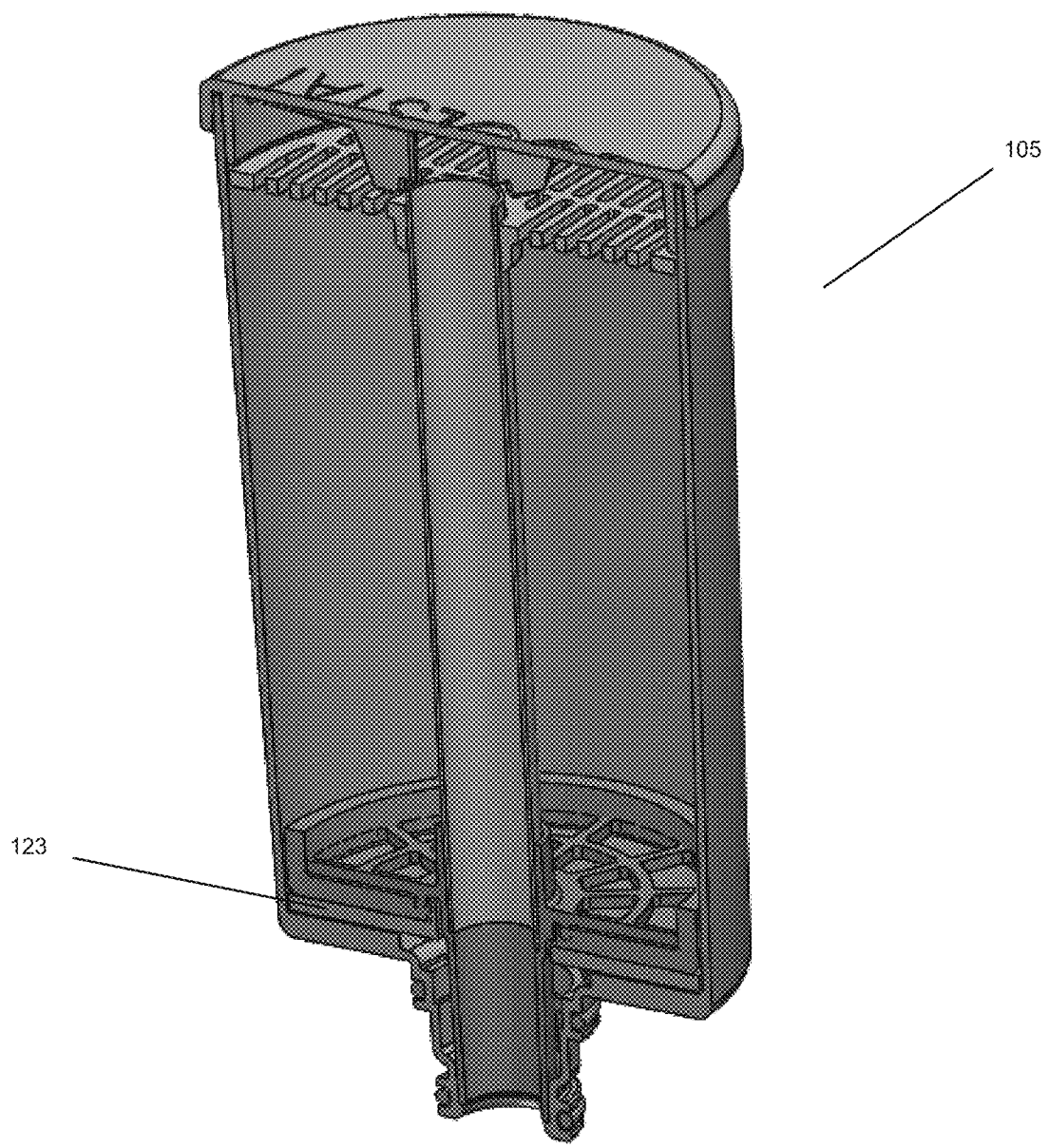
FIG. 8 shows cutaway views of the desiccant cartridge.
Figure 9:
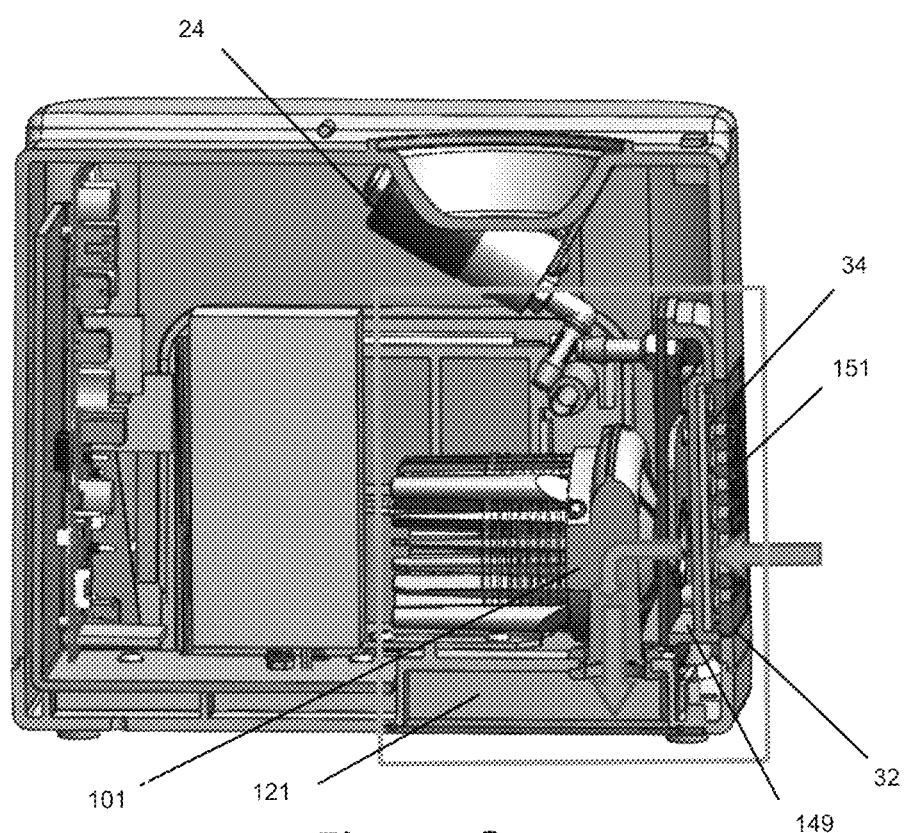
FIG. 9 is a cutaway view of a back end of a device according to an embodiment of the invention.

FIG. 8 shows an embodiment of a disposable cartridge 105 which may be composed of three primary components: a main body, a cap, and a central "straw". There may also be a mesh to contain the desiccant material (so it cannot leak out of the cartridge), an assembly to capture a high efficiency bacterial/viral filter 123, and a pair of O-rings to create a seal between the disposable cartridge and the device. To assemble the cartridge, the top cap is removed and the straw with filter assembly is placed into the body and held in place by a friction fit. Ribs may be provided to act as standoffs, holding the filter assembly slightly above the bottom of the cartridge. In addition to adding strength to the body, these ribs may also offset the mesh above the body surface, allowing for greater airflow. The desiccant material is then poured into the body, then the top mesh may be placed on top of the molecular sieve at the location shown in FIG. 8. Finally, the cap is snapped on or otherwise attached. The O-rings are preferably configured to mate with a pair of female features in the device, creating radial seals that separate the inlet from the outlet.

A detection switch 139 is triggered when the desiccant cartridge 105 is fully inserted. When this switch is open, the system will not turn on the blower 101 because the airflow path is not complete. The switch is positioned such that it will always trigger when the desiccant is fully seated, but will not trigger when the cartridge is only partially installed, as the cartridge's O-ring seals are not reliable at that point and air may be able to bypass the cartridge or escape the device.

The desiccant material has a limited capacity to adsorb moisture. When it becomes exhausted, the cartridge must be replaced with one containing fresh desiccant material. The time to exhaustion is dependent on both the moisture content and flowrate of the incoming air.

The removal of moisture from the air by the desiccant cartridge 105 produces heat, with the air temperature at cartridge exit reaching temperatures in excess of 70° C. in some cases. To cool the air before it reaches the patient, a custom two-sided heatsink 106 is positioned downstream of the desiccant cartridge 105. The hot side 141 of the heatsink 106 is directly in the dry air stream. A fan 127 draws ambient air into the housing via second air inlet 132 and forces it across the other side 143 of the heatsink, cooling the dry air. The fan also has a built-in tachometer, allowing the speed to be actively controlled based on outlet air temperature. A flange 147 on the heatsink 106 separates the two airflows but allows the communication of heat across the flange. Due to the difference in temperature between the two airstreams, the heatsink 106 conducts heat away from the air on the primary (hot) side 141 and warms the ambient air provided by the cooling fan 127 on the secondary side 143. Once the cooling air has blown through the heatsink 106 and absorbed heat, it exits the device through vents in the device bottom.

The device is capable of connecting to a pressurized medical air source/tank with standard medical gas tubing and fittings as commonly found in hospitals and other medical settings. The medical air is dryer than ambient air in most cases. A solenoid valve 24 is opened automatically when the blower 101 is turned on. Air is supplied to this valve through a standard medical air hose. A ¼" NPT fitting 28 on the rear of the device is attached to the valve inlet 26 through a reducing fitting, and a medical air hose-compatible fitting (which interfaces with the medical air hose) is attached to the NPT fitting 28.

A built-in orifice in the valve 24 limits the airflow entering the device. Air exiting the valve 24 is directed into the inlet plenum 149 at the blower input through a section of tubing and then follows the air flow path described above with respect to ambient air supply. Since there is a small positive pressure in the filtered inlet plenum 149 when drawing from the pressurized wall air source, some air will be exhausted from the device through the inlet manifold grill 151.

Three pressure taps 153, two on base plate—lid and one on base plate—base, attach to pressure sensors 129 on the PCB via ⅛" ID PVC tubing. The tap directly preceding the end of the device airflow path connects to the outlet pressure sensor 129a. After passing through the blower 101, for the remainder of the airflow pathway the air is operating at higher pressure than the ambient environment (this is required for airflow). The pressure sensor 129a acts as a safety mechanism, ensuring the pressure does not rise to a level unsafe for the patient. The placement of the pressure sensor 129a is conservative, as it is at the beginning of the tubeset 157. The airflow will drop in pressure over the course of the tubeset (due to tubeset resistance), and thus the measured value in the device will always be higher than that which the patient experiences.

The other two pressure taps 153 connect to a sensor 129b measuring the pressure differential across the desiccant cartridge to calculate flowrate.

In addition to the tap for the outlet pressure sensor 129a, a humidity sensor 133 and pair of thermistors 131 are also positioned by the airflow path outlet. Grommets ensure that air is not able to escape around these sensors. The air may experience a temperature drop as it passes through the tubing, as the air inside the device is almost always either hotter than or equal to ambient temperature. As the air passes through the tubeset, it is surrounded by ambient air, which will almost always be cooler than or equal to airstream temperature. Some amount of energy will be transferred to ambient through the tubing walls, cooling the air stream. The only case in which air temperature would rise while passing through the tubeset is when air stream temperature is lower than ambient temperature, in which case the air stream will never heat up to a temperature higher than ambient temperature.

The air delivered to the patient is filtered at three separate locations: the inlet filter 34 at the entrance to the device; the desiccant filter 123 after passing through desiccant material, and the patient filter (Disposable Manifold Filter) 109 upon exiting the device and entering the tubeset. The desiccant filter 123 and the patient filter 109 are contained within disposable elements, and will be replaced for each patient when new disposable elements are used.

Figure 12:
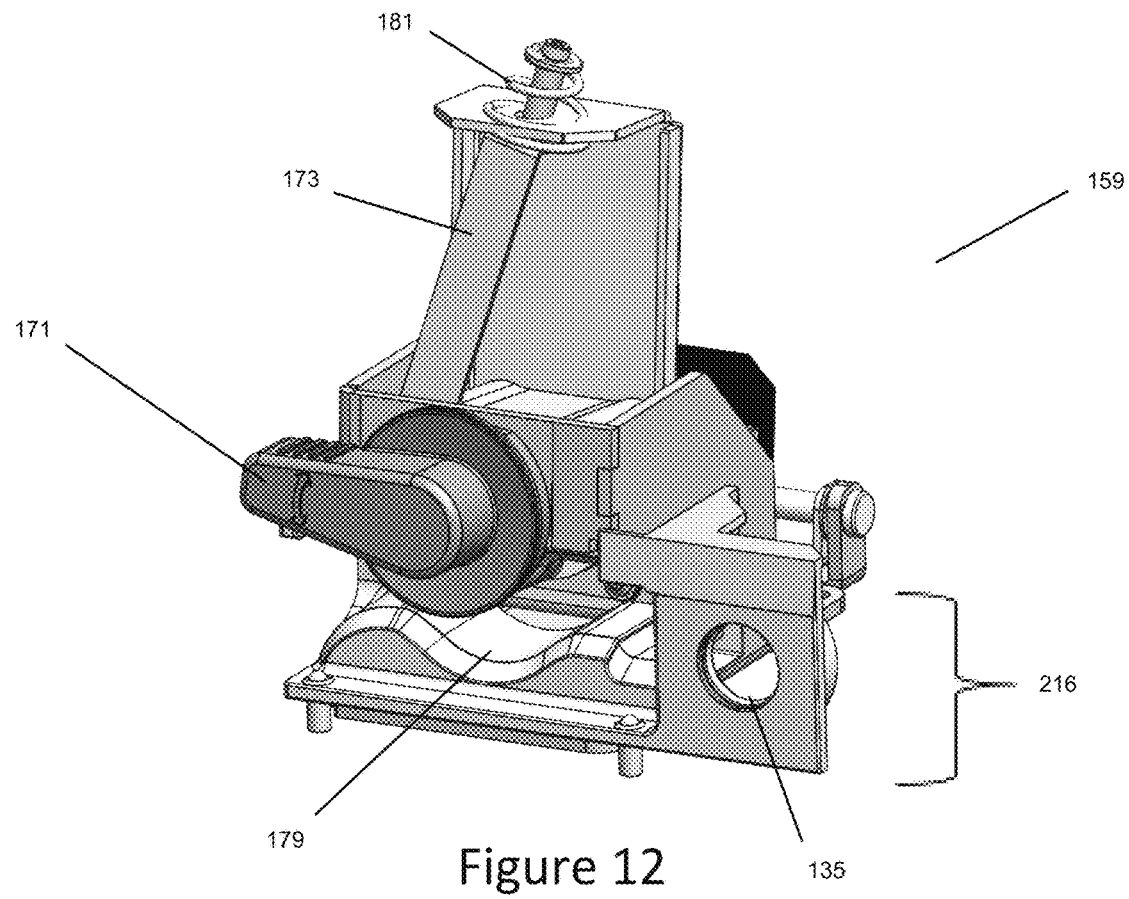
FIG. 12 is a three-dimensional front perspective view of a fluid pump assembly according to an embodiment of the invention
Figure 13:
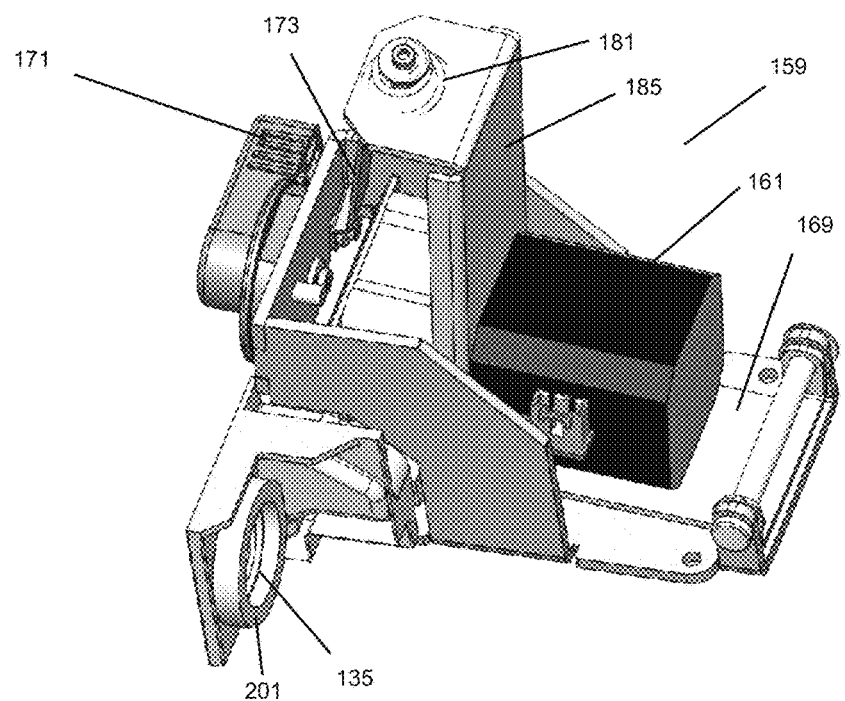
FIG. 13 is a three-dimensional top and side perspective view of a fluid pump assembly according to an embodiment of the invention.
Figure 14:
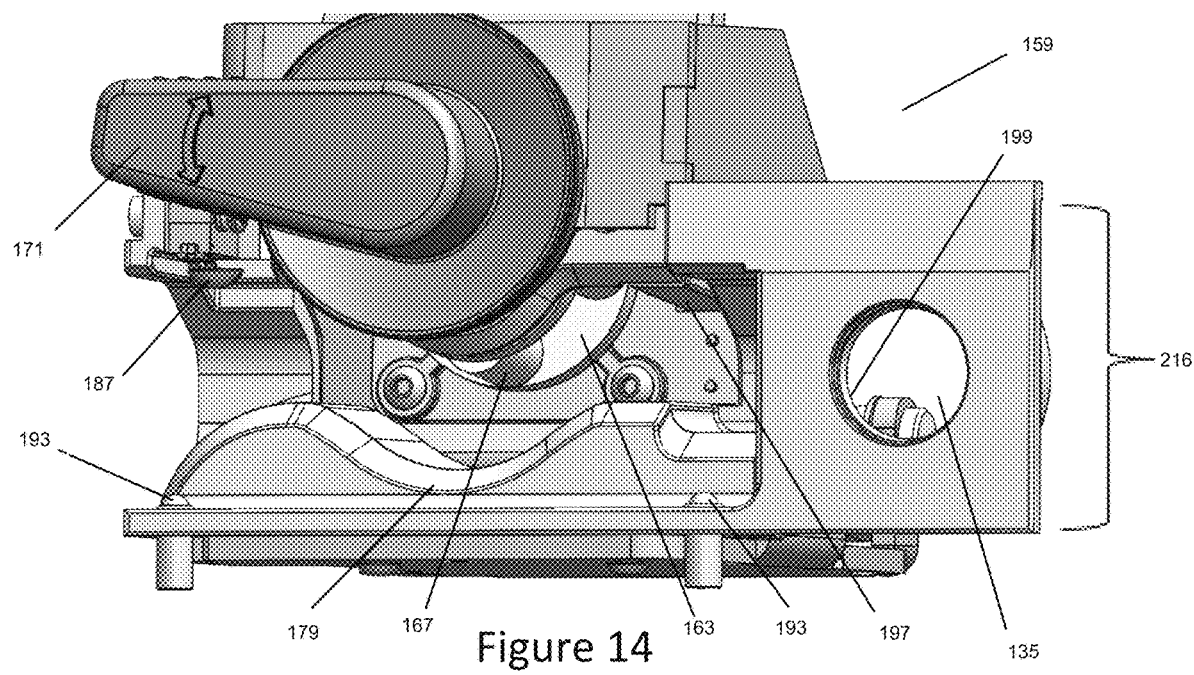
FIG. 14 is a three-dimensional close-up front perspective view of a fluid pump assembly according to an embodiment of the invention.
Figure 15:
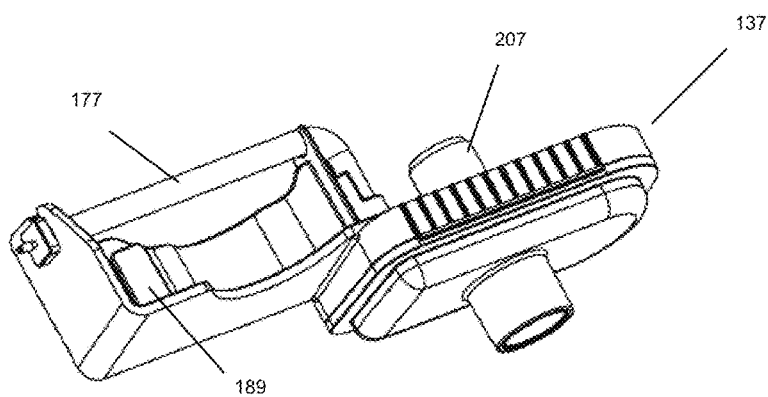
FIG. 15 is a perspective view of a manifold cartridge according to an embodiment of the invention.
Figure 16A:
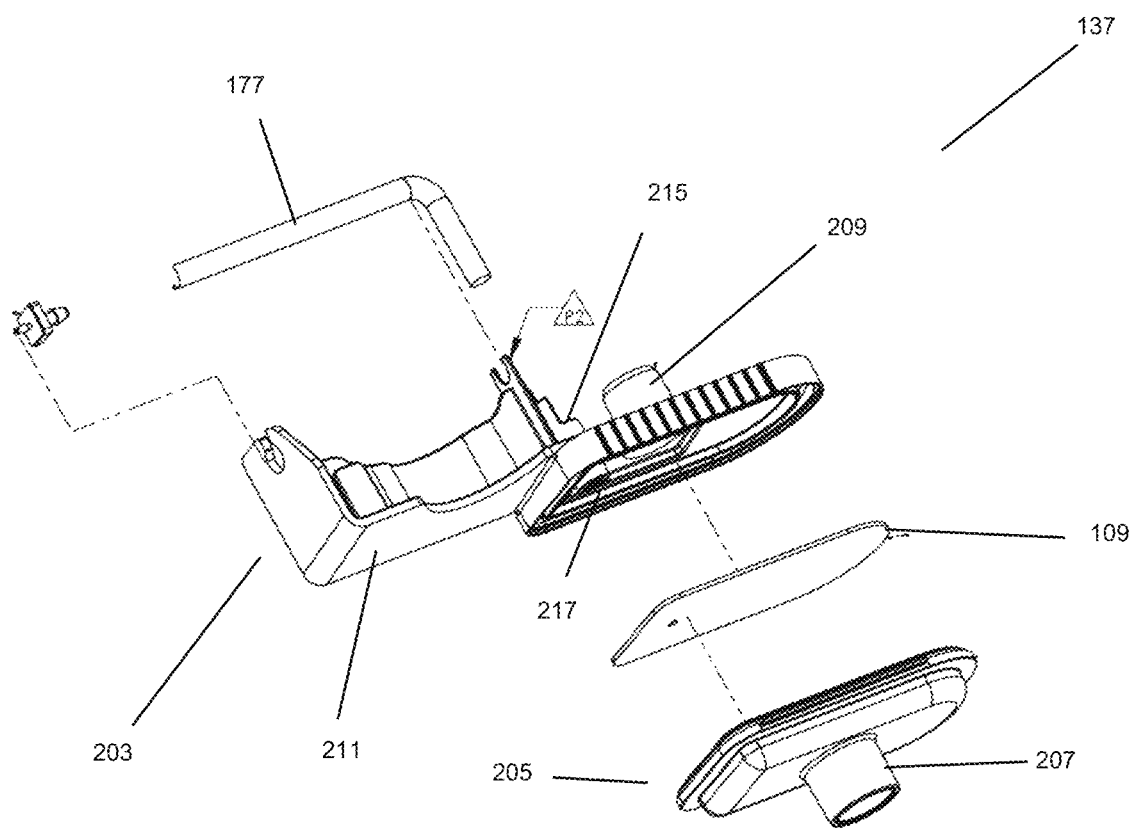
FIG. 16a is an exploded perspective view of the manifold cartridge shown in FIG. 15.
Figure 16B:
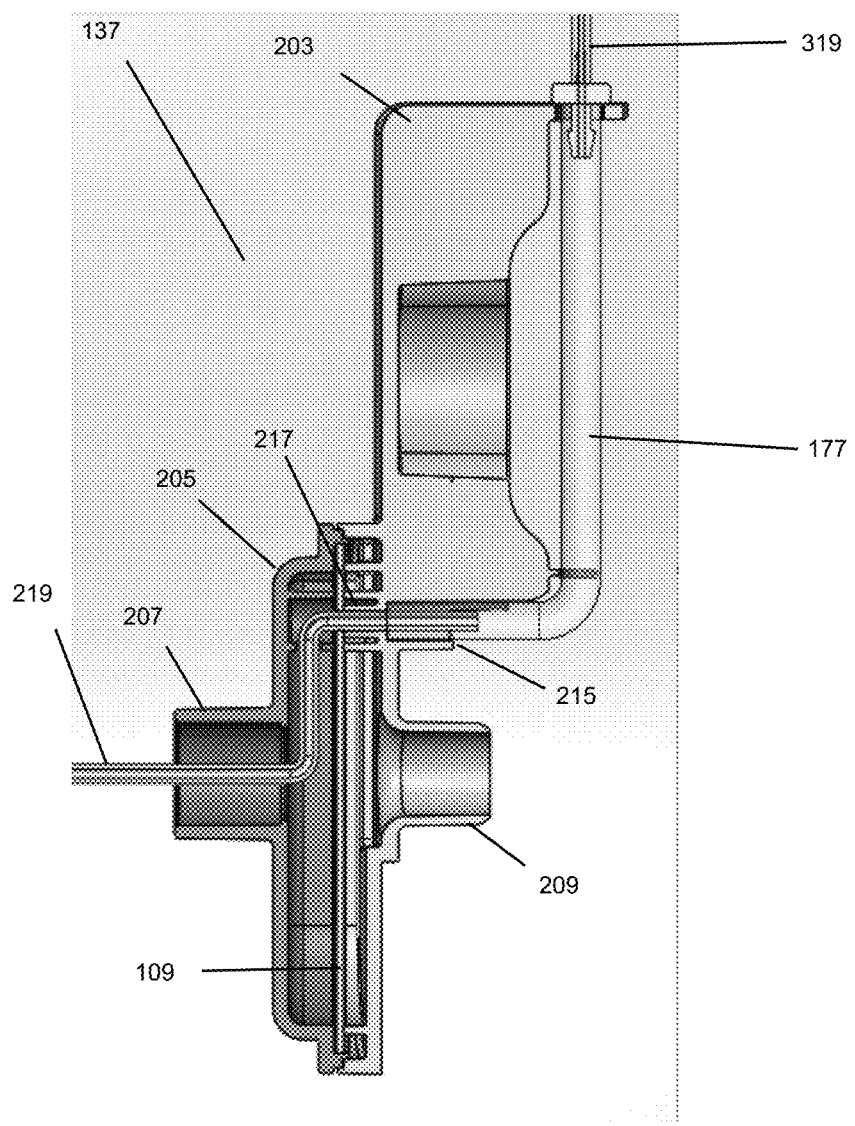
FIG. 16b is a cutaway view of the manifold cartridge showing the connection between the water delivery line, the transfer tube and the water supply line.
Figure 17:
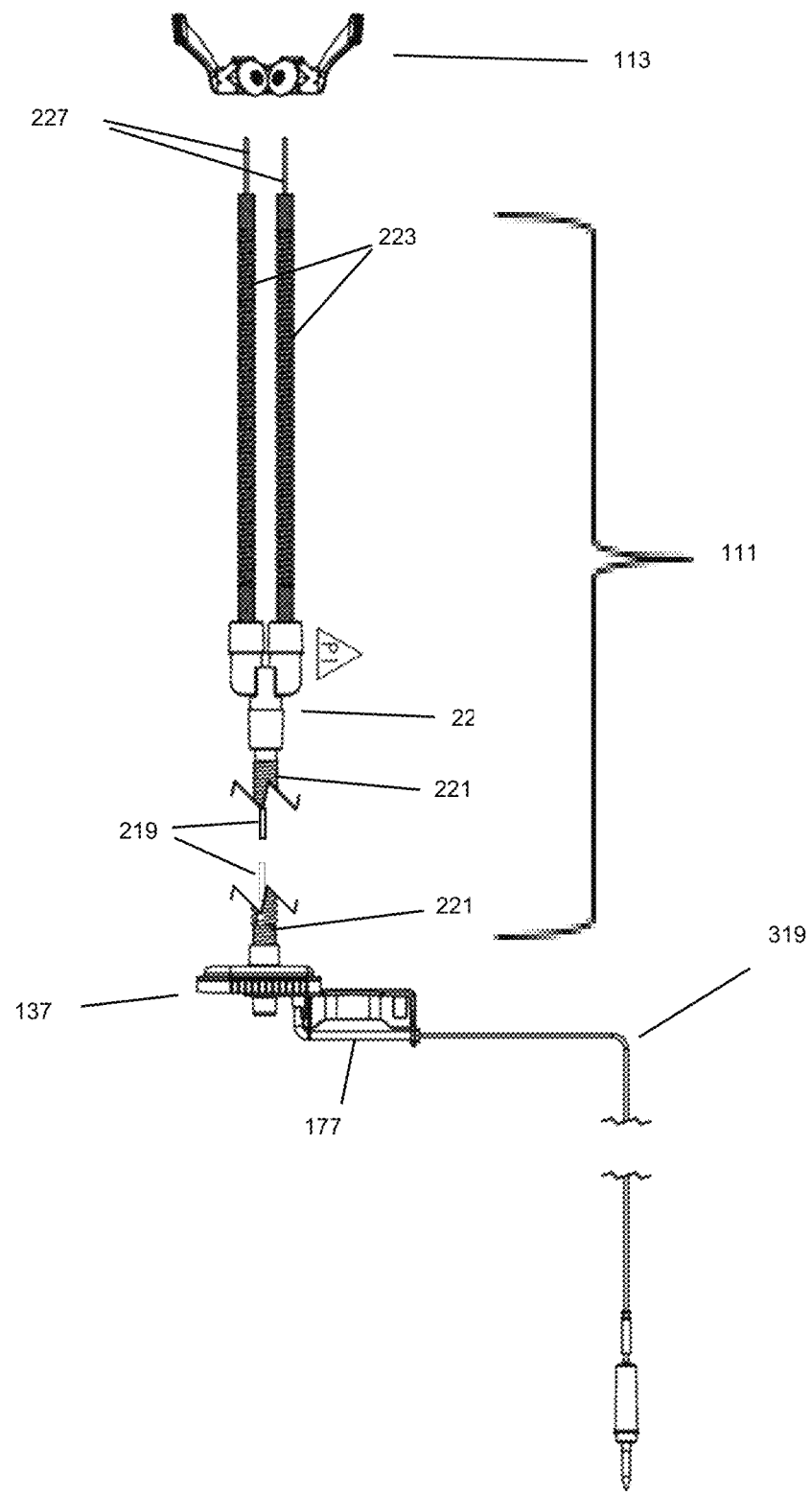
FIG. 17 is an assembly view of the disposable patient set, specifically, a manifold cartridge assembly attached to a tubeset (an air delivery tube containing within its lumen an isolated a water delivery tube) which in turn is connected to a patient interface device.
Figure 18:
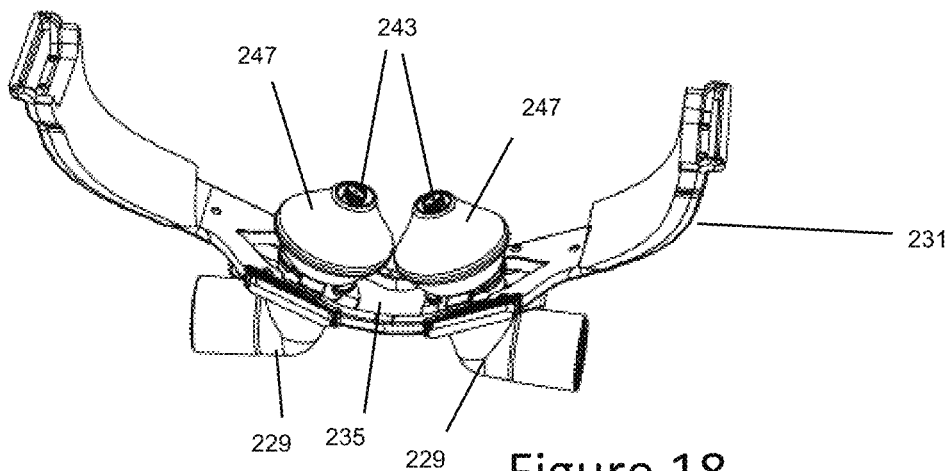
FIG. 18 is a top perspective view of a combined air and water delivery patient interface device according to an embodiment of the invention.
Figure 19:
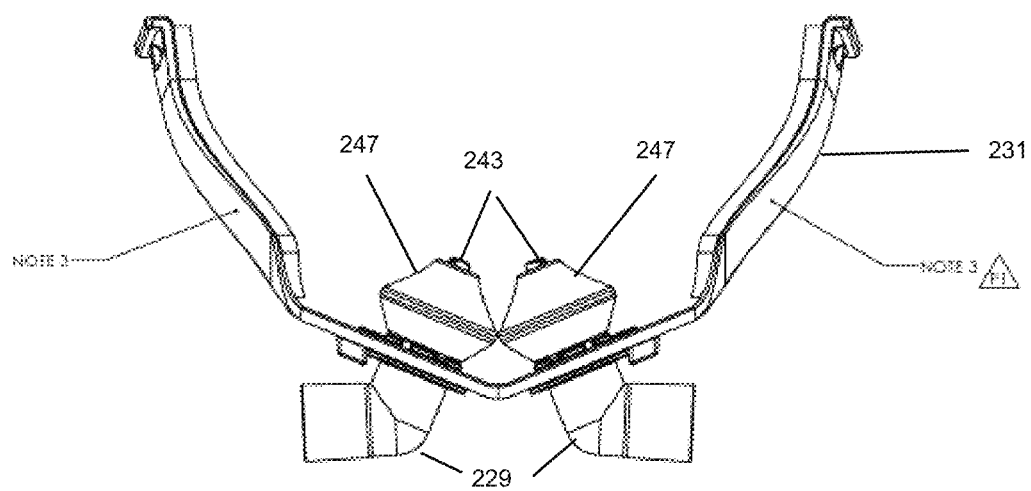
FIG. 19 is a front view of a combined air and water delivery patient interface device according to an embodiment of the invention.
Figure 20:
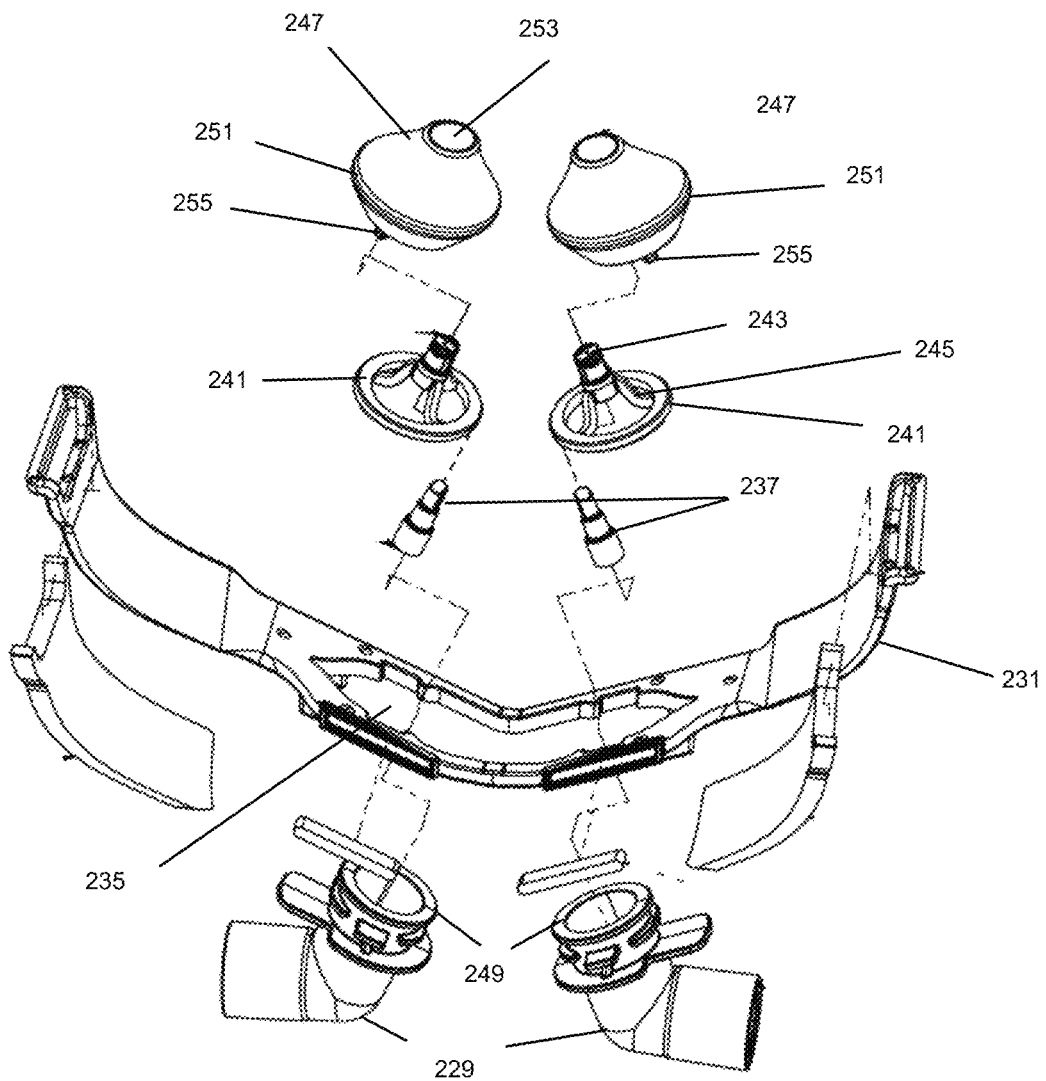
FIG. 20 is an exploded view of a combined air and water delivery assembly patient interface device according to an embodiment of the invention.

The fluid pump assembly 159, shown in FIGS. 12-14, provides the interface between the peristaltic pump 160 and the disposable manifold cartridge 137 for saline dispensing. The pump 160 is composed of a stepper motor 161 and matching pump head 163. Two bearings in the pump head provide translational support but allow rotation of the pump rotor 165 and its four free-spinning rollers 167. The pump is mounted onto a hinged plate 169, and positioned using a rotary knob 171 and linkage 173. A ball detent 175 behind the knob 171 helps to maintain the pump position when it is fully opened or closed. When closed, the linkage 173 is in an over-center position, keeping it securely fastened when upward force is applied by the section of tubing 177 it has engaged.

The knob 171 rotates approximately 100°, from roughly the 9 o'clock position when opened to the 6 o'clock position when closed.

The pump rotor 165 forces the tubing 177 from its horizontal alignment into a curved profile dictated by the pump platen 179. The tubing is clamped between the rollers on the pump rotor and the platen, fully occluding the tubing and preventing flow in either direction when the pump is stationary. A spring 181 between the linkage 173 and pump mount 185 makes the loading of the tubing 177 force-based rather than displacement-based, which improves reliability and reduces wear.

The assembly also includes two inputs. First, a lever-arm limit switch 187 to detect when the disposable manifold 137 is installed. The limit switch 187 is triggered by a small cantilevered rib 189 on the disposable manifold cartridge 137. This rib is purposely biased upwards to ensure that it reliably makes contact with the limit switch 187. The rib length has been optimized to ensure that the switch is not triggered until the manifold is fully installed. Two ball spring plungers 193 protruding up from the bottom of the assembly interface with detents in the disposable manifold 137 and cause the manifold to snap into place, reducing the variability of manifold placement and preventing the manifold from unintentionally slipping out of place when the knob is open.

Figure 21:
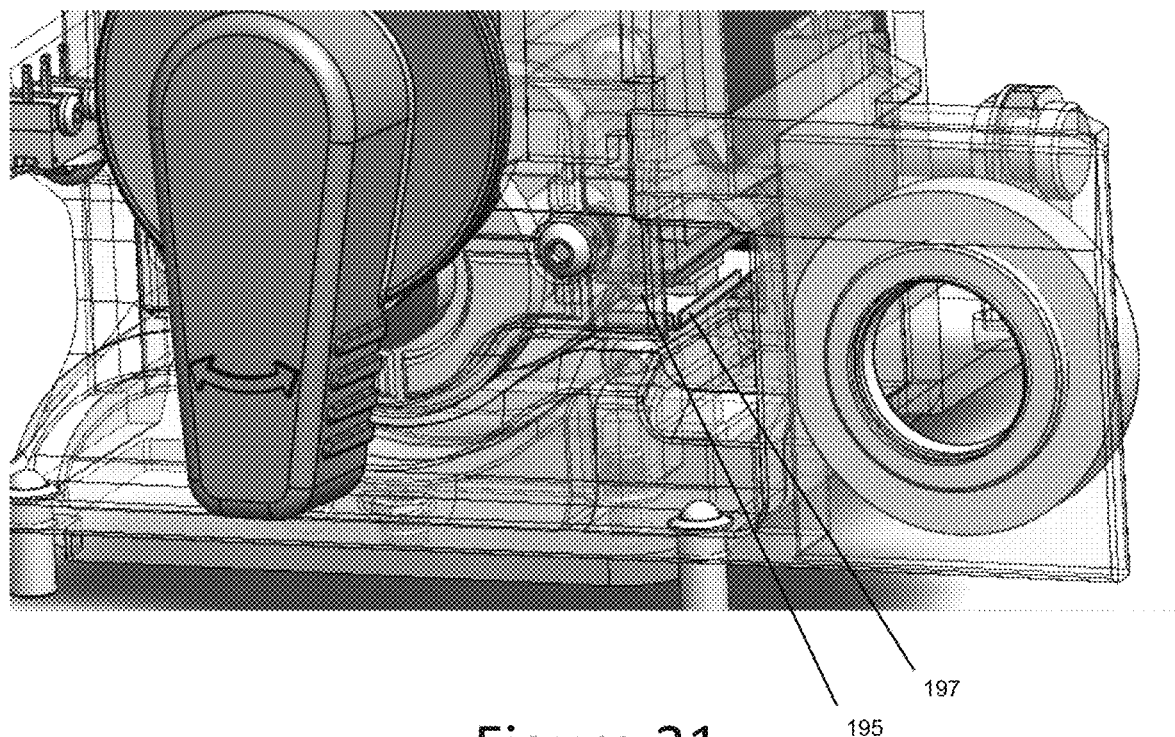
FIG. 21 is a three-dimensional close-up front perspective view of a fluid pump assembly according to an embodiment of the invention in which the forward most elements of the pump assembly housing are shown in phantom.

In addition to the limit switch, the assembly also contains the occlusion sensor 195 which is a small force transducer mounted on a basic PCB (see FIG. 21). The top side of a thin stainless steel plate 197 is pressed against the transducer. When the knob is closed, the bottom side of the plate 197 is pressed against the pump tubing, translating the force to the occlusion sensor. This is used to examine the pressure in the tubing during dispenses and determine whether each dispense was successful. This is possible because a successful dispense creates a distinct pressure profile. The plate's flat profile and cantilever mounting also help to compensate for any variation in the pump tubing alignment.

The occlusion sensor 195 is capable of detecting various error cases, such as leaks, occlusions, and air in the line. In the case of an empty source container, the device can use the sensor to determine when the line has been successfully re-primed. The occlusion sensor 195 also serves as a means to detect when the pump is latched down, as the tubing becomes compressed at this point and thus applies a force to the sensor (no force is applied to the sensor when unlatched).

The pump platen 179 provides an appropriate surface to support and position the tubing 177 during pumping, but it also serves two ancillary functions. The limit switch 187 and ball spring plungers 193 are mounted to it, and it also creates a sealed airflow path from the device to the manifold 137. This is accomplished with one gasket and one grommet. The first is a rod-wiper type rubber grommet 199 in a steel housing, which creates a radial seal with the manifold. The second is a foam face seal gasket 201 that seals the platen to the airflow path in the base plate.

The manifold cartridge 137 preferably has a base part 203 and a lid part 205, each of which have a device side and a side that faces away from the device (an away side). The away side of the base part 203 faces the device side of the lid part 205, and when connected, the base part 203 and the lid part 205 define a space 206 between them, which preferably contains an air filter 109. The away side of the lid part 205 has an air delivery port 207 for connecting to an air delivery tube 221. The device side of the base part 203 has an air receiving section 209 configured to fit snugly into the air outlet 135 of the housing via rubber grommet 199 and a water supply section 211 configured to interface with the fluid pump. The water supply section 211 includes a disposable flexible transfer tube 177 configured to connect to an independent water supply, e.g., a saline bag, at one end via water supply tube 319 and connected to a water transfer port/opening 215 in the device side of the base part 203. When the manifold cartridge 137 is inserted into the complimentarily shaped interface 216 in the device housing, the rotary fluid pump engages the flexible transfer tube 177. When the fluid pump is activated, the rotating arm of the rotary fluid pump rotates, squeezing the flexible transfer tube 177 against a curved surface (the platen 179) of the fluid pump causing fluid in the fluid supply to be drawn into and forced through the transfer tube 177. The water transfer port 215 in the device side of the base part 203 is connected to a corresponding water transfer port 217 on the away side of the base part. A water delivery tube 219 is connected to the device side water transfer port and travels through the space 206 between the base part and the lid part (through a small hole in the air filter, if provided) and out through the air delivery port 207, into the air delivery tube 221. That is, the air delivery tube 221 is sized to fit snugly onto or inside of the air delivery port 207. The water delivery tube 219 exits the air delivery port 207 and travels through the inside of the air delivery tube 221, thereby independently delivering isolated streams of dry air and water to the patient. According to an alternative embodiment, the water delivery tube 219 may be arranged so that it does not pass through the air filter At some point before it reaches the patient, the air delivery tube 221, containing within its lumen the independent and isolated water delivery tube 229, preferably bifurcates to provide two separate distal air delivery tubes 223. The bifurcation of the air delivery tube can be accomplished according to any known means, including a one-to-two connection element 225 Similarly, and preferably at about the same location, the single water delivery tube 219 is similarly bifurcated into two separate distal water delivery tubes 227, each of which continues to travel within a corresponding distal air delivery tube.

The distal air delivery tubes 223 terminate at bridge connectors 229 which connect to a slot in bridge 231 in which they can translate from side to side. The bridge 231 is preferably a flexible plastic strip configured to rest on or just above a patient's top lip, just beneath the nose, and preferably extending on either side of the nose resting against the patient's face to a point between the patient's cheek bones and ears. Opposite ends of the bridge 231 are adapted to receive an adjustable strap assembly 233 that goes around the back of the patient's head to hold the bridge 231 to the user's face. The center portion of the bridge defines one or more slots 235 to receive neck portions of the bridge connectors 229, allowing them to slide back and forth to accommodate different nose sizes/nostril separation distances.

The ends of the distal water delivery tubes 227 are fitted with nozzle adaptors 237 which in turn are connected to nozzle components 239 each comprising a ring-shaped base 241 and a central nozzle 243 connected to the ring-shaped base 241 by a three or more upwardly extending spokes 245 that support and center the nozzle. Nozzle components 239 and nozzle adaptors 237 are preferably press fit together and the interface between them creates a swirl chamber geometry that generates spray. The nozzle assemblies 239 are connected to the distal ends of respective bridge connector 229 by flexible elastomeric nasal pillows 247. The bottom opening 255 of the nasal pillows are sized to stretch fit over the distal end of the bridge connectors 229 just above where they interface with the bridge 231. The distal ends of the bridge connectors 229 are preferably formed with an outwardly extending flange 249 to better secure the elastic bottom neck of the nasal pillows. The bottom ring portion 241 of the nozzle component 239 rests in a wide but short shoulder portion 251 of the nasal pillow 247 that tapers to openings at the bottom end 255 and top end 253, respectively, and the pillow and nozzle assembly are sized so that the top of the nozzle component 239 extends through the center of the opening 253 at the nozzle end of the pillow without contacting the edges of the pillow opening. In this fashion, the water stream and the air stream are completely isolated from one-another until the point of delivery.

In various embodiments, the device may further include additional features that allow for the introduced fluid to be exhausted from the bodily fluid-containing cavity; see U.S. patent application Ser. No. 13/579,370 paragraph [0047], which is incorporated herein by reference.

The device may include a number of additional features to assist in regulating gas flow and pressure to achieve fluid elimination, anatomic or systemic cooling, energy removal, metabolic rate adjustment and/or weight loss. The device may further include a temperature sensor and/or pressure sensor for dynamic feedback and control of the gas temperature, pressure, and gas flow; see U.S. patent application Ser. No. 13/579,370, paragraph [0057], which is incorporated herein by reference.

The duration of treatment will vary depending on the desired level of fluid elimination, anatomic or systemic cooling, energy removal, metabolic rate adjustment and/or weight loss.

Unless otherwise set forth herein, the embodiments described above are generally directed towards creating a positive pressure source to blow dry air into the nose and nasal turbinates, which induces the evaporative phenomenon. According to these embodiments, air enters through the nose and exits the mouth, and about 20 to 30 cm of water of pressure is generated in order to create the preferred air flow according to most preferred embodiments, but other embodiments use pressures up to 40 cm, 50 cm and 60 cm of water pressure.

However, testing using these embodiments has shown that as pressure is increased, the fine vasculature in the turbinates may be compressed, possibly causing a reduction in blood flow and water supply, which in turn could reduce the vascular supply of heat which is needed to support evaporative cooling. As such, evaporation (from any surface) and resulting heat removal could decrease as air pressure increases.

Accordingly, the present invention also includes the creation of air flow over the nasal turbinates through the use of a vacuum or other suction. According to these embodiments, two air tubes would be provided, one connected to each nostril. A negative pressure source (e.g., a fan) or vacuum source is connected on one side to pull dry air into the other side. The dry air enters a first nostril, travels across one side of the turbinates, and goes out the other nostril (the side with the negative pressure source). This negative pressure/vacuum source also causes vasodilation, which could improve the vascular supply of heat and thus improve the evaporative model, even beyond normal respiratory conditions. This embodiment of the invention has an additional benefit in that the user need not be concerned about venting from the mouth; that is, the mouth need not be kept open. This embodiment is also unaffected by possible occlusions in the upper airway, which could block air flow according to other embodiments. According to a preferred embodiment, the fan or vacuum causes air to be drawn through a desiccant cartridge prior to entering the first nostril. According to another embodiment, a blower may be provided at the inlet side so that the net gage pressure across the turbinates is very low or zero, with the positive pressure fan/blower and the negative pressure vacuum source balancing one-another out. According to another embodiment, a blower may be provided at the inlet side on one nostril and open to atmosphere on the other. According to embodiments where a vacuum source is provided at one nostril, a seal may be placed between the inlet nostril and the inlet tube to prevent or inhibit the entry of ambient (non-desiccated) air from entering the inlet nostril.

Although the invention has been described with reference to the above example, it will be understood that modifications and variations are encompassed within the spirit and scope of the invention. Accordingly, the invention is limited only by the following claims.

What is claimed is:

1. A device for inducing evaporation of a fluid from a bodily fluid-containing space in a mammal, the device comprising, in an integrated unit:
   an air delivery subassembly comprising:
      an air inlet,
      an air outlet,
      an air flow path connecting said air inlet and said air outlet,
      an air inlet sensor configured to measure air temperature or pressure or both;

a blower situated in said air flow path and configured to draw ambient air from said air inlet and force said ambient air through said air flow path and out said air outlet, a desiccant chamber situated in said air flow path and configured to receive a desiccant element;

a heat sink situated in said air flow path and configured to remove heat added to air in said air flow path during removal of moisture from said air by said desiccant element;

an air outlet sensor configured to measure air temperature or pressure or both;

a liquid delivery subassembly comprising:

a liquid pump, configured to interface with a liquid supply tube and to force liquid to be drawn into said liquid supply tube from a liquid source and out an outlet of said liquid supply tube;

wherein said air delivery subassembly and said liquid delivery subassembly maintain isolation between said air flow path and said liquid supply tube so that air in said air flow path and liquid in said liquid supply tube do not come into contact at any time prior to delivery to said mammal, wherein at least a portion of said liquid supply tube is attached to a manifold cartridge, and wherein said liquid pump defines an interface configured to receive and engage said manifold cartridge for alignment of said liquid supply tube with said liquid pump.

2. A device according to claim 1, wherein said liquid pump comprises a peristaltic rotary pump.

3. A device according to claim 1, further comprising a heat sink fan to blow ambient air across a portion of said heat sink that is not in contact with said air flow path.

4. A device according to claim 1, wherein said liquid pump further comprises pressure sensors to determine presence of liquid in said liquid supply tube and a pressure of liquid in said liquid supply tube.

5. A device for inducing evaporation of a fluid from a bodily fluid-containing space in a mammal, the device comprising, in an integrated unit:

an air delivery subassembly comprising:
 an air inlet,
 an air outlet,
 an air flow path connecting said air inlet and said air outlet,
 an air inlet sensor configured to measure air temperature or pressure or both;
 a blower situated in said air flow path and configured to draw ambient air from said air inlet and force said ambient air through said air flow path and out said air outlet,
 a desiccant chamber situated in said air flow path and configured to receive a desiccant element;
 a heat sink situated in said air flow path and configured to remove heat added to air in said air flow path during removal of moisture from said air by said desiccant element;
 an air outlet sensor configured to measure air temperature or pressure or both;

a liquid delivery subassembly comprising:
 a liquid pump, configured to interface with a liquid supply tube and to force liquid to be drawn into said liquid supply tube from a liquid source and out an outlet of said liquid supply tube;

wherein said air delivery subassembly and said liquid delivery subassembly maintain isolation between said air flow path and said liquid supply tube so that air in said air flow path and liquid in said liquid supply tube do not come into contact at any time prior to delivery to said mammal, said device further comprising a second air inlet connected to a solenoid valve for receiving pressurized air from a pressurized air source, said portable device further comprising a supplemental air flow path connecting said solenoid valve to said blower.

6. A device for inducing evaporation of a fluid from a bodily fluid-containing space in a mammal, the device comprising, in an integrated unit:

an air delivery subassembly comprising:
 an air inlet,
 an air outlet,
 an air flow path connecting said air inlet and said air outlet,
 an air inlet sensor configured to measure air temperature or pressure or both;
 a blower situated in said air flow path and configured to draw ambient air from said air inlet and force said ambient air through said air flow path and out said air outlet,
 a desiccant chamber situated in said air flow path and configured to receive a desiccant element;
 a heat sink situated in said air flow path and configured to remove heat added to air in said air flow path during removal of moisture from said air by said desiccant element;
 an air outlet sensor configured to measure air temperature or pressure or both;

a liquid delivery subassembly comprising:
 a liquid pump, configured to interface with a liquid supply tube and to force liquid to be drawn into said liquid supply tube from a liquid source and out an outlet of said liquid supply tube;

wherein said air delivery subassembly and said liquid delivery subassembly maintain isolation between said air flow path and said liquid supply tube so that air in said air flow path and liquid in said liquid supply tube do not come into contact at any time prior to delivery to said mammal, said device further comprising a manifold cartridge comprising:
 a manifold air inlet and a manifold air outlet connected by a manifold air flow path,
 a liquid supply flow path comprising said liquid supply tube attached to and supported in said manifold cartridge and configured to be connected at one end to a liquid source, said liquid supply tube comprising a section of tubing that enters and passes through said manifold air flow path and exits said manifold cartridge through said manifold air outlet.

7. A device according to claim 6, wherein said integrated unit comprises an interface for receiving said manifold cartridge in which said manifold air inlet is received in said air delivery subassembly air outlet, and wherein said liquid pump defines a recess configured to receive and engage a portion of said manifold cartridge holding said liquid supply tube.

8. A device according to claim 7, further comprising a locking mechanism for reversibly locking said manifold cartridge into said interface and recess.

9. A device according to claim 8, further comprising an air delivery tube configured to be connected at one end to said manifold air outlet and connected at a second end to a patient interface assembly, said air supply tube comprising a lumen in which is located a liquid delivery tube in fluid communication with said liquid supply tube in said manifold cartridge, and wherein air flow in said air delivery tube is isolated from and does not come in contact with liquid in said liquid delivery tube.

10. A device according to claim 9, further comprising a patient interface assembly comprising a harness configured to rest against a patient's lip just beneath the nostrils, said harness defining one or more slots configured to slidaby receive two tube connectors, said tube connectors each attached at a distal end to respective hollow elastomeric nasal pillows having a bottom opening connected to a respective tube connector and a top opening for delivery of air to a patient's nostrils, said nasal pillows each supporting within an interior space a nozzle assembly connected to a respective water delivery tube.

11. A device according to claim 10, wherein said nozzle assembly is arranged so that a distal tip of said nozzle assembly extends outside of said nasal pillow top opening a distance of 2-10 mm.

12. An apparatus for independently delivering isolated air and water streams to nostrils of a patient comprising a harness configured to rest against a patient's lip just beneath the nostrils, said harness defining one or more slots configured to slidaby receive two air delivery tube connectors said air delivery tube connectors each attached at a distal end to respective hollow elastomeric nasal pillows having a bottom opening connected to a respective tube connector and a top opening for delivery of air to a patient's nostrils, said nasal pillows each supporting within an interior space a nozzle assembly connected to a respective water delivery tube, said nozzle assembly arranged so that a distal tip of said nozzle assembly extends outside of said nasal pillow top opening a distance of 2-10 mm.

* * * * *